(12) United States Patent
Jensen et al.

(10) Patent No.: US 8,740,969 B2
(45) Date of Patent: Jun. 3, 2014

(54) APPARATUS FOR AND METHOD OF FITTING A STENT-GRAFT OR SIMILAR DEVICE

(75) Inventors: Kim Moegelvang Jensen, Koevenhavn SV (DK); Bent Øhlenschlaeger, Li. Skensved (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1498 days.

(21) Appl. No.: 12/378,313

(22) Filed: Feb. 13, 2009

(65) Prior Publication Data
US 2009/0204199 A1 Aug. 13, 2009

Related U.S. Application Data

(60) Provisional application No. 61/065,536, filed on Feb. 13, 2008, provisional application No. 61/069,115, filed on Mar. 12, 2008.

(51) Int. Cl.
*A61F 2/06* (2013.01)

(52) U.S. Cl.
USPC .......................... 623/1.23; 623/1.11; 606/205

(58) Field of Classification Search
USPC ................................. 623/1.11, 1.23; 606/205
See application file for complete search history.

(56) References Cited

U.S. PATENT DOCUMENTS

| | | | |
|---|---|---|---|
| 4,913,141 A | 4/1990 | Hillstead | |
| 6,280,464 B1 * | 8/2001 | Hayashi | 623/1.11 |
| 6,974,471 B2 * | 12/2005 | Van Schie et al. | 623/1.12 |

FOREIGN PATENT DOCUMENTS

| | | |
|---|---|---|
| WO | WO 94/16629 | 8/1994 |
| WO | WO 99/30763 | 6/1999 |
| WO | WO 2006/047520 | 5/2006 |
| WO | WO 2006047520 A2 * | 5/2006 |

OTHER PUBLICATIONS

Intn'l Search Report, PCT/US2009/000863, May 28, 2009, EPO.
Written Opinion, PCT/US2009/000863, May 28, 2009, EPO.

* cited by examiner

*Primary Examiner* — Victor Nguyen
*Assistant Examiner* — Kevin Everage
(74) *Attorney, Agent, or Firm* — Richard J. Godlewski

(57) ABSTRACT

A fitting device (104) for fitting a stent-graft (100) into a lumen of a patient includes a catheter (110), a cannula (112) reciprocably carried in the catheter (110) and a pair of gripper claws (106) in the cannula (112). The gripper claws (106) grip onto a stent (102) at the proximal end (128) of the stent-graft (100) which a suture loop (108) is tied to a stent (102) at an intermediate position along the stent graft (100). The stent-graft (100) can be curved by pulling the end-most stent (102) backwards, that is by retracting the cannula (112) into the catheter (110) while the gripper claws (106) grip onto the stent (102). The proximal end of the stent-graft (100) can also be adjusted position-wise by moving the cannula (112) into and out of the catheter (110). Thus, precise positioning and curving of the stent-graft (100) can be achieved.

7 Claims, 6 Drawing Sheets

APPARATUS FOR AND METHOD OF FITTING A STENT-GRAFT OR SIMILAR DEVICE

CROSS-REFERENCE TO RELATED APPLICATIONS

This application claims priority of provisional application Ser. No. 61/065,536, filed Feb. 13, 2008 and provisional application Ser. No. 61/069,115, filed Mar. 12, 2008.

TECHNICAL FIELD

The present invention relates to apparatus for and a method of fitting a stent-graft, stent or other device into a lumen of a patient, particularly into a highly curved lumen such as the aortic arch and into locations which provide little room for error in the placement of the device, such as lumens having short necks of healthy vascular wall.

BACKGROUND ART

Prostheses for the repair of vascular defects, including for example vascular aneurysms, are well known in the art. A common prosthesis for treatment of such a medical condition is a stent-graft.

Prostheses of this type are typically deployed endoluminally through a vein or artery adjacent a surface of a patient. For example, aortic prostheses are commonly fed through the femoral artery. A common method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into the aortic arch of a patient.

Even though such a procedure is possible into the aortic arch, it is mired in difficulties as a result of the tight curvature of the latter. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus of a less than effective treatment. Furthermore, as a result of the non-optimal placement of the stent-graft using known procedures, there is a limit to the length of neck of healthy vascular wall which is needed to provide a seal around the proximal end of the stent-graft. This limits the application of such stent-grafts, in particular for the treatment of aneurysms close to a branch vessel. In addition, in some instances at least, a part of the proximal end of the stent-graft can remain loosely located in the vessel, leading to premature fatigue failure and thrombus effects.

Attempts have been made to resolve these difficulties. For instance, in the applicant's U.S. Pat. No. 6,974,471, mechanisms are described for imparting a curvature to the stent-graft at the moment of its deployment.

The deployment of stent-grafts and other devices, particularly in the aortic arch, in lumens having short necks of healthy vascular wall and other difficult pathologies also requires very precise placement of the device to ensure a good coupling to healthy tissue and in particular a coupling which has longevity and which provides a fluid tight seal with the vessel wall. Prior art systems do allow for a certain amount of coarse re-positioning of the device, for example by pulling on the proximal end of the device. However, if the device is either fitted too far downstream or pulled too much during fitting, the procedure needs to be repeated, for example by withdrawing the device back into its delivery introducer and starting the deployment operation afresh. Repeating the procedure increases operating time, trauma to the patient and still does not guarantee a successful outcome. In some instances, it is necessary to abort the procedure.

DISCLOSURE OF THE INVENTION

The present invention seeks to provide and improved system for and method of fitting a stent-graft or other device to a patient.

According to an aspect of the present invention, there is provided apparatus for fitting an implantable medical device into a lumen of a patient including a carrier provided with a proximal end and a distal end, wherein the distal end is provided with first and second spaced holding elements each able to holding releasably to first and second structural elements of a device, the carrier being adjustable so as to alter the spacing between the first and second holding elements.

Preferably, the holding elements are tie elements tying the carrier to the implantable medical device.

The ability to adjust the relative positions of the first and second tie elements allows both an adjustment to the form and shape off the device as it is being fitted and also allows a repositioning of the device, both on the proximal and the distal directions.

Advantageously, the proximal end of the carrier includes a proximal manipulation element operable for adjusting the carrier within a patient, the proximal manipulation element providing for movement of the distal end of the manipulation element in backward and forward directions.

In practice, the first tie element is tied to or adjacent a proximal end of a stent-graft or other device to be fitted to a patient, that is the end furthest from the surgeon and typically upstream in the direction of blood flow, while the second tie element is attached to an intermediate position on the device or to its distal end, that is the downstream end.

Adjustment of the tie elements in a direction which reduces the spacing between them can in practice provide for a reduction in the length of the device held by the tie elements and as a result can cause the device to curve in the direction of the tie elements, by pulling on one side at the proximal end of the device. Adjustment of the tie elements in a direction to increase the separation therebetween can push the proximal end of the device in an upstream direction.

Similarly, the carrier can be moved such that both tie elements are pushed or pulled together, thereby allowing for precise adjustment of the proximal end of the device in a patient. This is particularly useful in the placement of the device where there is little room for error.

Preferably, the first and second tie elements are co-operatively linked such that the first tie element must be released from the device before the second tie element can be released.

In the preferred embodiment, the first tie element includes at least two gripper claws able to grip onto a structural element of a device, such as a stent or other strut-like element. The gripper claws are configurable between open and closed positions. Preferably, the gripper claws are provided in a cannula, wherein in a retracted position the gripper claws are in their closed position while in an extended position the gripper claws are in their open position.

The second tie element is, in the preferred embodiment, a looped or hooked element able to hook to a structural element of a device, such as a stent or other strut-like element. Most preferably, the looped or hooked element is in the form of a suture loop attached to the device, the suture loop being releasable from the carrier so as to release the device from the carrier.

The carrier may be made of stainless steel, an alloy of metal or a polymer material. The gripper fingers are preferably made of stainless steel, spring steel or any other suitable material.

According to another aspect of the present invention, there is provided a method of fitting a stent-graft or other implantable medical device in a patient by means of fitting apparatus as taught herein, including the steps of locating the device within a lumen of a patient, moving at least one of the proximal end and an intermediate position of the device along the lumen by adjustment of the position of the first and/or second tie elements so as to place the device in the lumen and releasing the first and second tie elements so as to release the device in the lumen.

Preferably, the method includes the step of adjusting the position of the first and second tie elements relative to one another so as to curve the device during fitting.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

For the purposes of this disclosure, when used in connection with description of a stent-graft or other implantable device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

Figure 1:
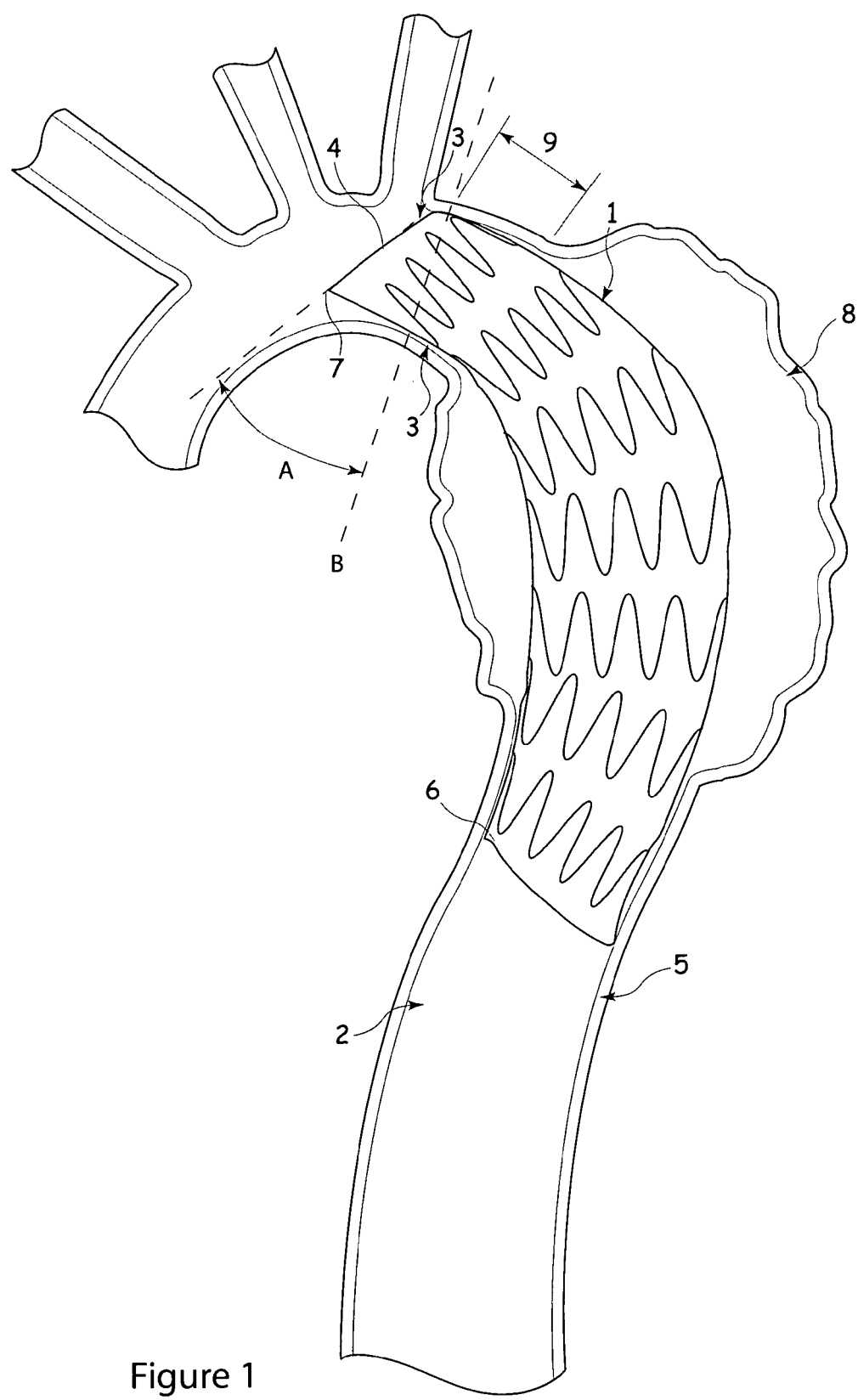
FIG. 1 shows an example of stent-graft deployed in the aortic arch by a prior art method.

Referring to FIG. 1, there is shown an example of deployment of a stent-graft 1 within the aorta 2 of a patient for the treatment of, for example, an aneurysm 8. In this particular example, the stent-graft extends part-way into the aortic arch 3 at its proximal end 4, down to the thoracic aorta 5 at its distal end 6. The curvature of the aortic arch 3, coupled with use of a conventional introducer system which follows the arch 3 by being bent thereby, can cause the proximal end 4 of the stent-graft 1 to be located incorrectly, that is not to have its opening perpendicular with the vessel at that position. As a result, the inner side 7 of the stent-graft 1 stands proud of the vessel wall, being spaced therefrom. The angle A at which the proximal end 4 lies deviates from the perpendicular line B. The resultant gap between the inner side 7 and the aortic wall provides a path for leakage of blood, which can lead to failure of the stent-graft in achieving its intended function. In practice, such imprecise deployment results in it being necessary to have a relatively long neck 9 to achieve a reliable seal between the stent-graft 1 and the vessel wall. Thus, medical conditions which do not have a sufficient length of neck 9, that is of healthy vessel wall, cannot at present be treated.

In addition to these problems, the end 7 of the stent-graft tends to flap in the force of blood flow, leading to fatigue wear and to thrombus formation.

Figure 2:
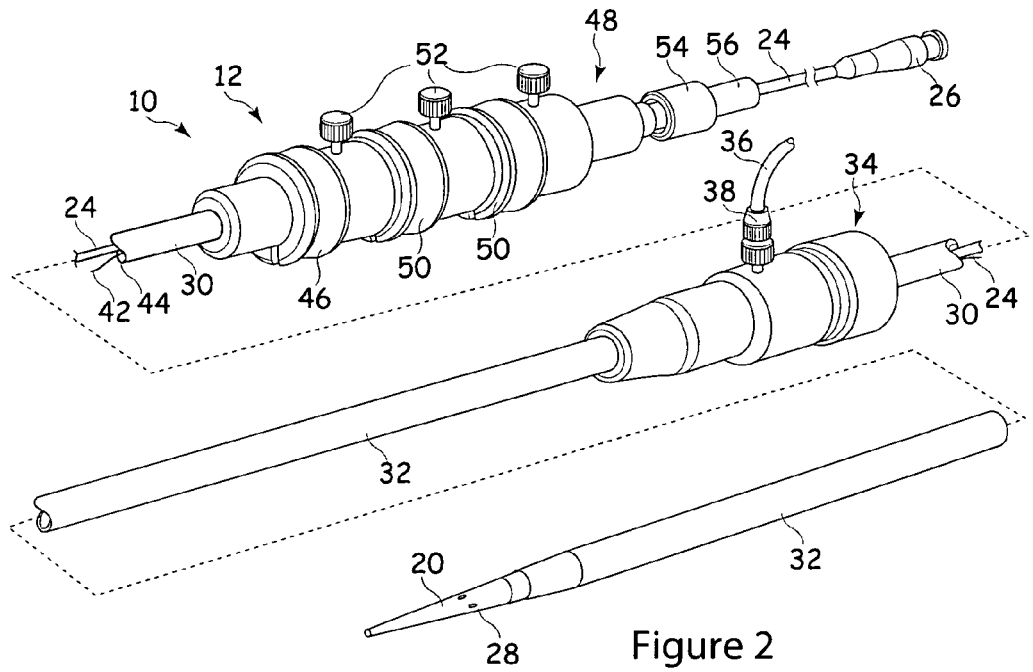
FIGS. 2 and 3 are perspective views of an example of introducer system which can be used with the present invention.
Figure 3:
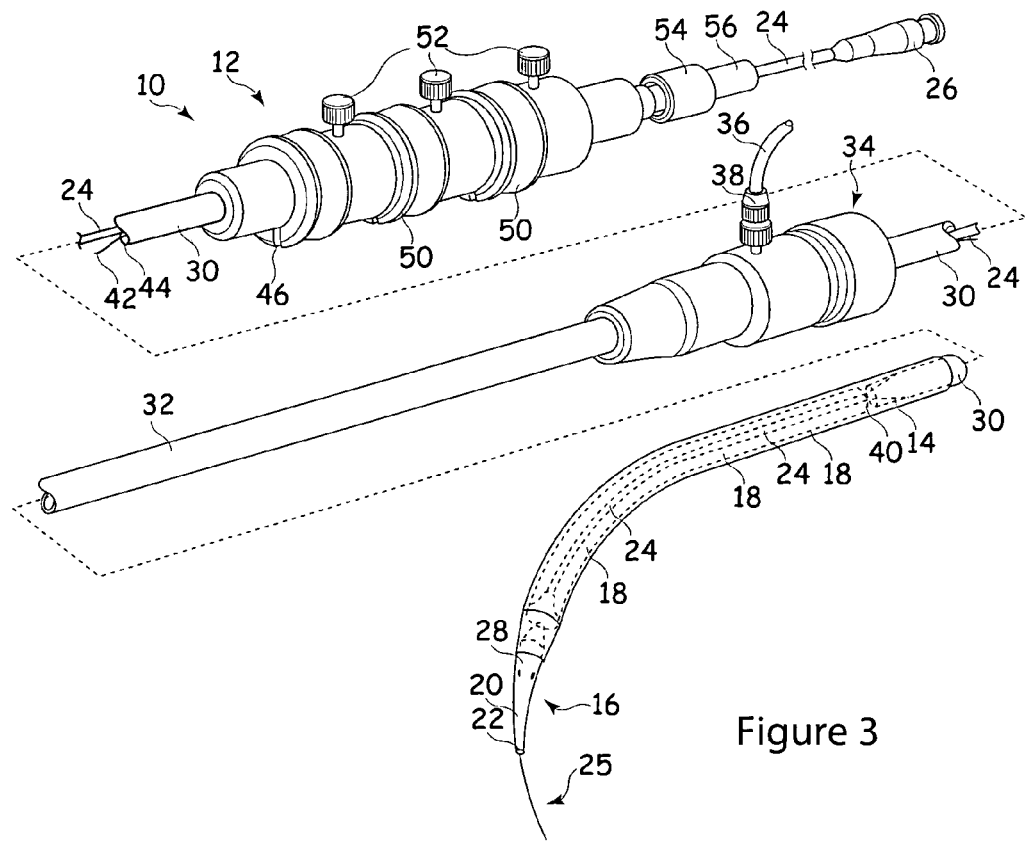

Referring now to FIGS. 2 and 3, there is shown an example of introducer of the type used in the deployment of stent-grafts of the form shown in FIG. 1. The introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire 25 of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

As will be apparent in particular from FIG. 3, the distal end of the introducer is flexible, so as to be able to follow a tortuous path of a patient's vasculature, as well as in some applications to locate a stent-graft in a curved portion of a lumen such as the aortic arch. The distal end curves, however, by being pulled into this configuration as a result of curving of the guide wire, which is itself urged into a curved shape by the curvature of the lumen. As a result of this, the distal end of the introducer tends to follow the outside of any curve. When deployment occurs in such a situation, as it does in the aortic arch for example, the stent-graft can become improperly located, as in the example of FIG. 1.

The applicant's earlier U.S. Pat. No. 6,974,471 describes a variety of mechanisms for imparting a curvature to the stent-graft at the moment of its deployment, primarily by mechanisms which act to pull on the proximal (upstream) end of the stent-graft.

The present invention seeks to address the problem with prior art introducer systems and in a way which does not alter the assembly of the stent-graft or add significantly to the components of the introducer device. Moreover, the preferred embodiments provide a system which can enhance the fitting of the stent-graft into a lumen, particularly at the aortic arch and other highly curved regions of vasculature.

Another problem with prior art introducer systems is that they provide little adjustability of the position of the device in the lumen of the patient. If the device is incorrectly positioned, it must generally be withdrawn, typically by compressing this again into the delivery sheath, and the placement procedure commenced again. This does not, however, guarantee success on the subsequent occasion and does not provide any added precision. In the case of delivery devices which allow for a certain amount of adjustability of the proximal end of the device, such as that described in U.S. Pat. No. 6,974,471, this is only in a single direction, that is distally or downstream.

Figure 4:
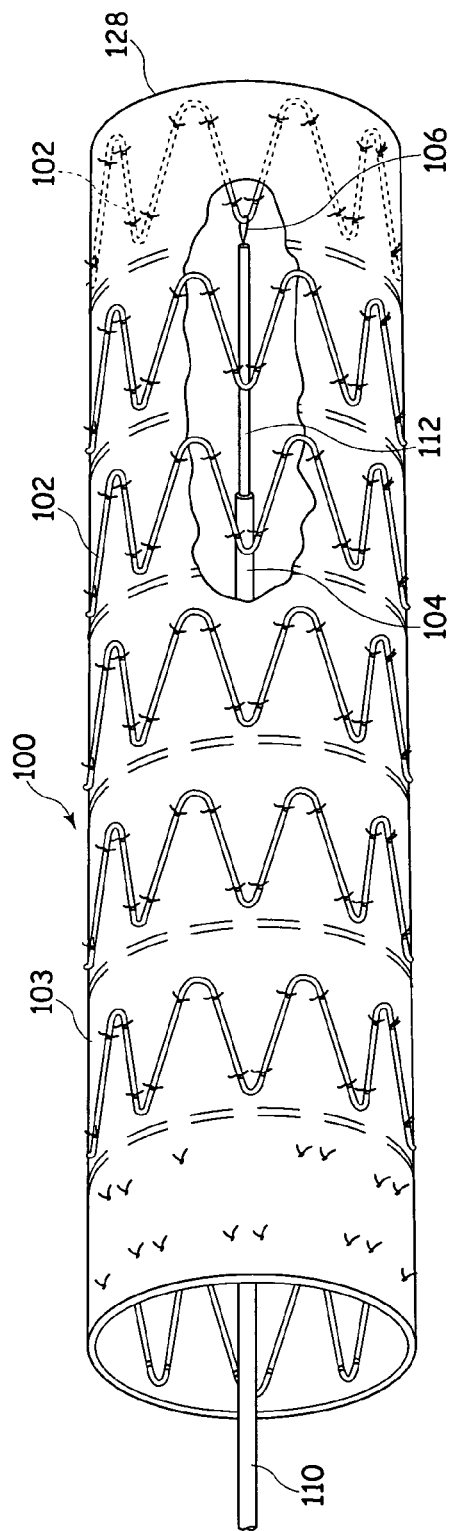
FIG. 4 shows a partially cut-away side elevational view of a stent graft attached to a delivery system in accordance with a preferred embodiment of a fitting apparatus in accordance with the present invention.
Figure 5:
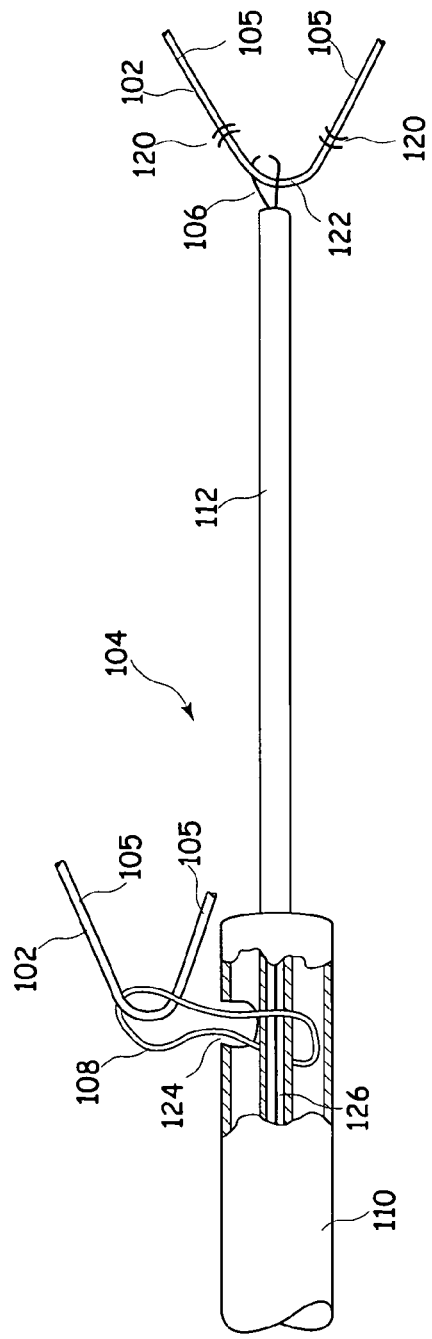
FIG. 5 shows an enlarged view of the delivery system of FIG. 4.

Referring now to FIGS. 4 and 5, there is shown in schematic form a preferred embodiment of delivery assembly for fitting a stent-graft 100 into a lumen of a patient. In FIG. 4, part of the graft material of the stent-graft has been omitted from the drawing to show the relative location of the delivery assembly shown enlarged in FIG. 5. The stent-graft 100 has a conventional structure, that is provided with a plurality of stents 102 attached to a tube 103 of graft material. In this particular example, the stents 102 are attached by sutures, however the form of the device is not critical to the system and method taught herein.

The fitting device 104 is in this example located within the stent-graft 100 and includes a pair of gripper claws 106 at a distal end thereof. The gripper claws 106 are such as to grip onto the end-most stent 102 of the stent-graft 100, in this example at the meeting point 122 of two adjacent stent struts 105, that is at the valley (or peak) formed at the position in which the two adjacent struts 105 join together. This stent 102 is closest to the distal end 128 of the stent-graft 100. For this particular example of stent-graft 100, there is provided for stent attachment purposes a pair of sutures 120 located either side of the point 122 and passing through the graft material. The sutures 120 assist in providing a secure grip of the claws 106 to the stent 102 by preventing slippage of the latter along the stent struts 105.

The fitting device 104 also includes, in this embodiment, a loop 108 of suture thread, which is tied to a point between stent struts 105 of a stent 102 located in an intermediate position along the stent-graft 100. The suture loop 108 is, in this example, permanently tied to the stent 102 to as to remain even after deployment of the stent-graft 100.

The gripper claws 106 are reciprocably located in a cannula 112, which may be a flexible stainless steel cannula or formed of any other suitable material including a plastics material. The cannula 112 is itself reciprocably located in a catheter 110, which may be made of the same material as the cannula 112 or of any other suitable material.

At the distal end of the catheter 110 there is provided a slot or other opening 124 which gives access to the housed cannula 112 within the catheter 110. The loop 108 passes around the cannula 112 and it is by this that the loop 108 is fixed to the device 104.

Figure 6:
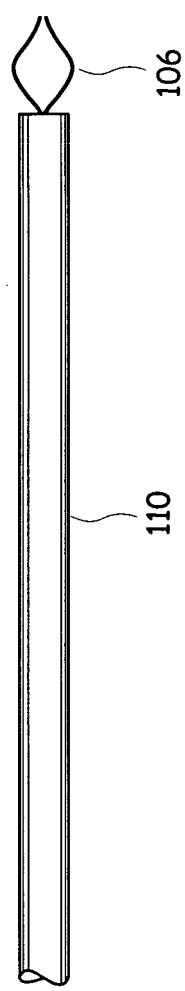
FIGS. 6 and 7 show in enlarged form a distal end of the delivery system of FIGS. 4 and 5 with gripper fingers thereof in extended and retracted positions.
Figure 7:
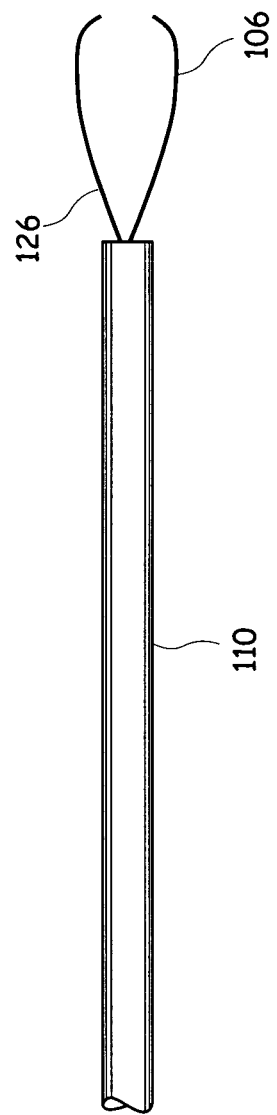

The claws 106 are formed at the distal ends of two wires 126 made of suitable material, such as spring steel, Nitinol or any other material. The wires 126 extend to the proximal, external manipulation, end of the device 104 and are coupled to a suitable handle device (not shown) which can be operated by a surgeon to move the wires 126 proximally and distally so as to pull the claws 106 inwards towards the distal end of the cannula 112 as shown in FIG. 6 and outwards, as shown in FIG. 7. In the retracted position, the internal wall of the cannula 112 acts to push the claws 106 in towards one another, thereby to grip an element located between these, while in the extended position, the claws can spring outwardly, as shown in FIG. 7, so as to configure the claws into a releasing position.

The handle device can be any of suitable type which allows for the gripper claws 106 and in particular the wires 126 to be pushed in a distal (into patient) direction and pulled in a proximal (out of patient) direction so as to control the configuration of the claws 106.

The fitting device 104 is typically fitted to the stent-graft 100 or other device at the point of assembly and then mounted to a suitable introducer assembly of a type analogous to that shown in FIGS. 2 and 3. Thus, the stent-graft 100 is compressed radially onto a delivery catheter together with the fitting device 104.

When the stent-graft 100 is positioned inside the patient, it is released from the outer sheath, such as sheath 32, and thus into a state in which it can expand, by itself or by means of an expansion balloon or the like. At this point, the stent-graft 100 can be adjusted in position and also in configuration to be located precisely in the appropriate part of the patient's vasculature and also configured to suit the anatomy of the vasculature at that point. For example, the device 104 can be pushed into the patient (distally) to move the stent-graft 100 upstream, or pulled proximally (out of the patient) to move the stent-graft 100 downstream. In this manner, the stent-graft can be positioned accurately in the patient's vasculature.

Furthermore, the stent-graft 100 can be made to curve, for example to conform to the curvature of the vessel into which it is to be fitted. This could, for example, be to conform to the curvature of the patient's aortic arch. The stent-graft 100 can be caused to curve by retracting the cannula 112 into the catheter 110 while the gripper claws 106 remain closed. This retraction pulls the stent 102 attached to the claws 106 towards the stent 102 attached to the suture loop 108 and thus contracts that side of the stent-graft 100. This contraction has the effect of curving the stent graft 100 in the direction of the side of the device connected to the fitting device 104. Given the flexibility of the wires 126, the cannula 112 and the catheter 110 (the latter not needing to be as flexible as the other elements of the device), these will also flex in curvature with the stent-graft 100.

The curvature of the stent-graft 100 can be increased or decreased as necessary by moving the cannula 112 into and out of the catheter 110, until the required curvature has been achieved and until the proximal end 128 has been precisely located in the patient's vasculature.

Once the stent-graft 100 is located as desired, the device 104 can be completely removed form the stent-graft 100. The first stage of the removal process releases the claws 106, by moving the wires 126 distally to the position shown in FIG. 7. Once opened as shown, the cannula 112 can be retracted to clear the claws 106 from the stent 102. Once cleared, if desired, the claws 106 can be retracted into the cannula 110, that is to the position shown in FIG. 6 but at this point not gripping anything.

The cannula 112 can be retracted all the way into the catheter 110, at least past the slot 124 but in some instances completely removed from the patient. Once the cannula 112 and gripper claws 106 pass the slot 124, the loop 108 becomes free of its restraint on the device 104 and thus releases the intermediate stent 102 from the fitting device 104. At this stage, the catheter 110 can also be removed from the stent-graft 100 and thus from the patient. Once so removed, the stent-graft 100 is fully deployed in the patient, in a precise position and with a curvature compatible with the vasculature.

Figure 8:
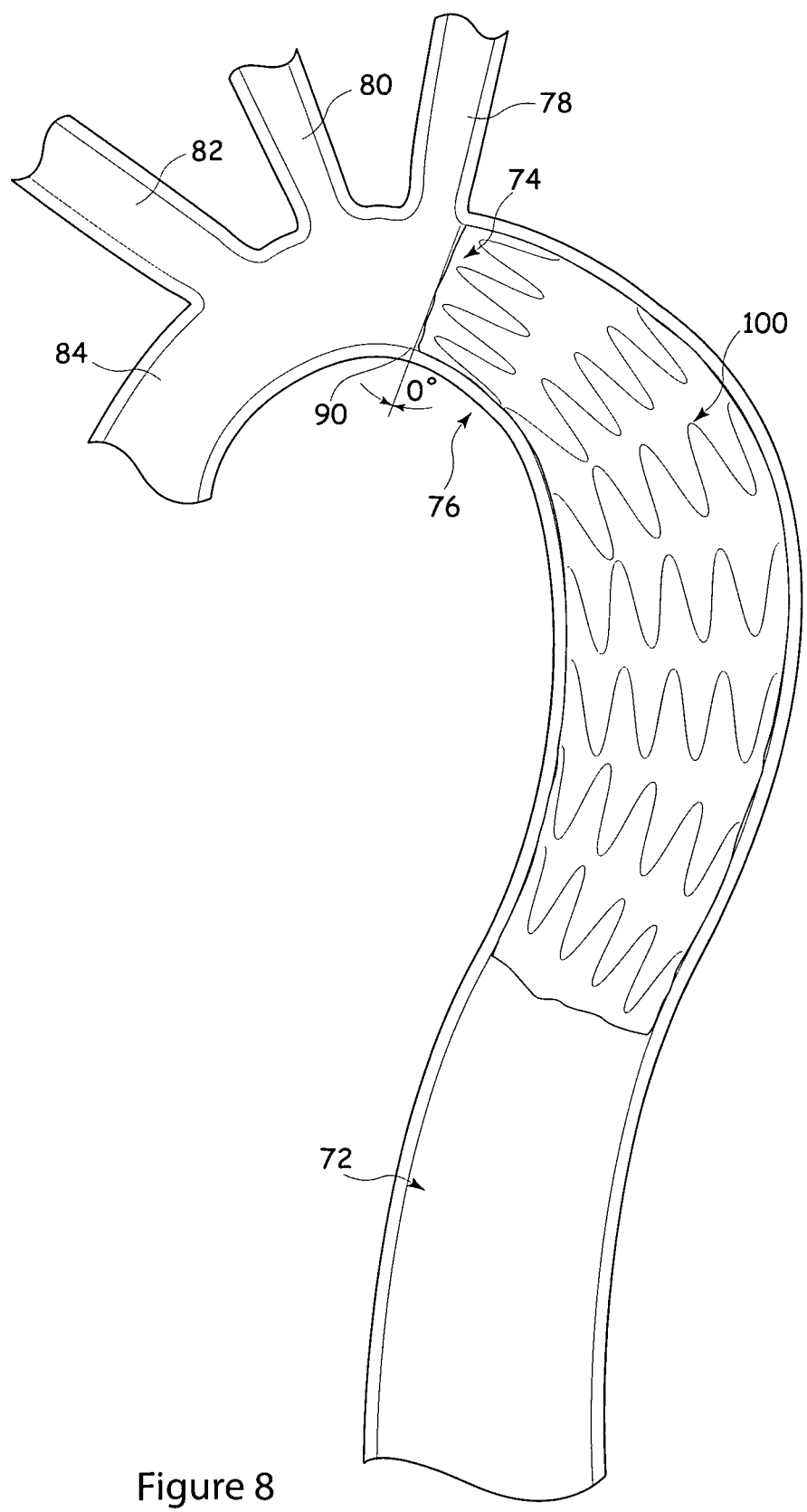
FIG. 8 shows the stent-graft when fully deployed.

The end result of the procedure is shown in FIG. 8. As can be seen, the stent-graft 100 is properly deployed in an aorta 72 of a patient. The proximal end 74 of the stent-graft 100 is positioned in the aortic arch 76, just short of the left subclavian artery 78, in this example. The introducer is equally suited to the deployment of a suitable stent-graft beyond the left subclavian artery 78, as well as beyond the left common carotid artery 80 and the brachiocephalic artery 82 and into the ascending aorta 84. Fenestrated or branched stent-grafts for such applications are known in the art. It will be noted that the proximal end 74 lies correctly so as to be perpendicular to the vessel wall, that is the plane of the opening of the proximal end of the stent-graft lies precisely transverse to the vessel so as to ensure that the proximal end of the graft tubing is parallel and precisely aligned with the walls of the vessel. In this manner, the stent-graft 100 is well sealed to the vessel wall all around its circumference, including at the radially internal side 90, leaving no gap for blood leakage.

The precise and reliable placement of the proximal end 74 of the stent-graft 100 can be effected in a much shorter neck length of vessel wall compared to the less reliable prior art systems. Thus, it is possible with this introducer system to fit stent-grafts and other prostheses and implants to patients who cannot be treated by current procedures, for example patients who suffer from aneurysms too close to a branch vessel or which otherwise have a very short neck length of healthy vessel wall. Furthermore, the introducer system taught herein allows the placement of stent-grafts and other devices in vessels having a much tighter curvature than can be achieved with existing systems.

Figure 9:
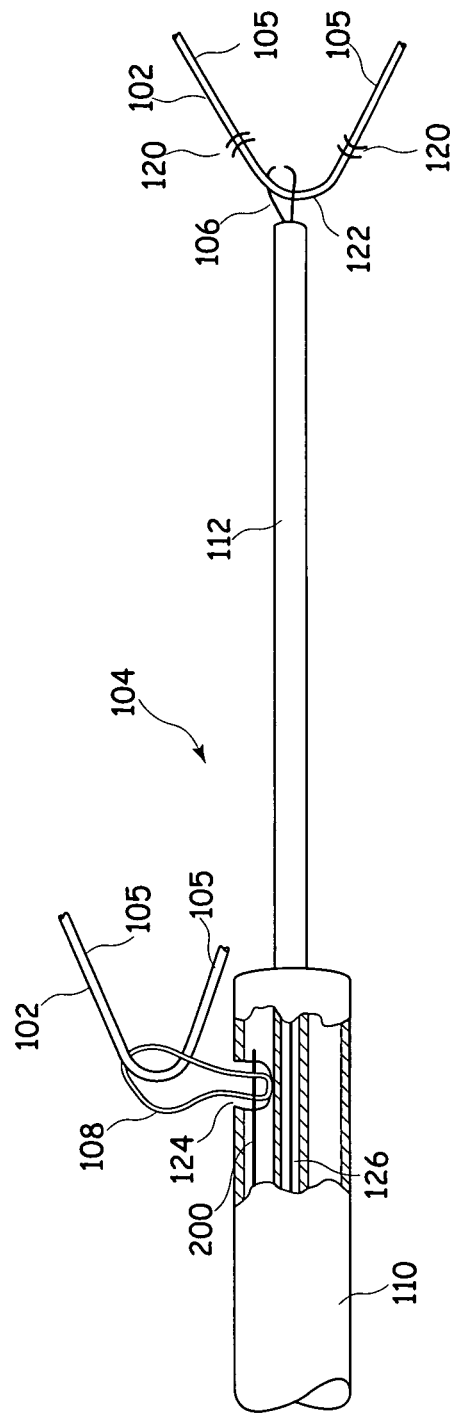
FIG. 9 shows another arrangement or holding the proximal suture loop.

Referring now to FIG. 9, there is shown another embodiment of fitting device 104', in which the loop suture thread 108 forming part of the second tie element is free of the cannula 112 but is held in place, that is tied to the catheter 110 by means of a restraining wire or rod 200, around which it is looped. The restraining wire or rod 200 extends through the catheter 110 to a proximal position of the introducer, that is to an external manipulation unit. In this example, the stent graft, to which a fitting device 104' is attached, can be positioned in a lumen of a patient and curved as required by pulling the cannula 102 and thus the gripper arms 106 to wards the second tie element 108. Once the stent graft has been positioned and curved as desired, the physician can release either of the tie elements 106, 108 in whatever order is most appropriate for the particular medical procedure. For example, the gripper arms could be first released and then the suture loop 108 released thereafter. Alternatively, the suture loop 108 can be released first by pulling back the tie wire or rod 200 and the gripper arms released thereafter. This implementation provides more deployment options for a position which may be advantageous in some medical procedures.

The fitting device 104 thus provides for very precise positioning of a stent-graft 100 or other device, allowing for adjustment of its position and its curvature to fit precisely in the lumen of the patient. The only element which may be retained on the stent-graft 100 is the small loop 108 of suture material, which will have no material effect on the performance of the stent-graft 100 or on the patient.

If desired, the suture loop 108 could be formed of a biodegradable and bio-compatible material of a type known in the art, thus leaving no element of the fitting device 104 after degradation of the suture loop.

The preferred embodiments have been described in connection with the deployment of stent-grafts into the aorta of a patient, particularly within the aortic arch. These embodiments can also be used for implanting other is medical devices into a patient, including but not limited to stents, vena cava filters, occlusion devices and so on.

What is claimed is:

1. Apparatus for fitting an implantable medical device into a lumen of a patient including:
    a carrier provided with a proximal end and a distal end;
    the distal end of the carrier including a first and a second spaced holding element each able to releasably hold a first and a second structural element of a device respectively, the second holding element being able to releasably hold the second structural element at a position on the device intermediate a first and second end thereof;
    the first holding element including at least two gripper claws movable between open and closed positions, wherein in a retracted position the gripper claws are in their closed position and while in an extended position the gripper claws are in their open position;
    a cannula for carrying the gripper claws;
    a catheter within the apparatus for carrying the cannula;
    a release element located within the cannula and operable to tie the second holding element thereto, the second holding element being releasable upon actuation of the release element;
    the second holding element is a loop of thread and the release element is a rod or wire; and
    the carrier being adjustable so as to alter the spacing between the first and second holding elements while the first and second holding elements releasably hold the first and second structural elements of the device respectively.

2. Apparatus according to claim 1, wherein the proximal end of the carrier includes a proximal manipulation element operable for adjusting the carrier within a patient, the proximal manipulation element providing for movement of the distal end of the manipulation element in backward and forward directions.

3. Apparatus according to claim 1, wherein the first and second holding elements are co-operatively linked such that the first holding element must be released from the device before the second holding element can be released.

4. Apparatus according to claim 1, wherein the first and second holding elements are independently releasable.

5. Apparatus according to claim 1, wherein the second holding element is releasably attached to the catheter.

6. Apparatus according to claim 1, wherein the second holding element is releasable from the catheter upon withdrawal of the cannula.

7. Apparatus according to claim 1, wherein the loop is releasable from the carrier so as to release a device from the carrier.

* * * * *